United States Patent
Arand et al.

[11] Patent Number: 6,021,349
[45] Date of Patent: Feb. 1, 2000

[54] DEFIBRILLATOR WITH AUTOMATIC AND MANUAL MODES

[75] Inventors: Patricia A. Arand, McMinneville; Nancy H. Forman, Beaverton; Jonathan N. Andrews, McMinneville, all of Oreg.

[73] Assignee: Agilent Technologies, Santa Clara, Calif.

[21] Appl. No.: 09/126,905

[22] Filed: Jul. 31, 1998

[51] Int. Cl.[7] ................................................ A61N 1/39
[52] U.S. Cl. ................................................................ 607/5
[58] Field of Search .................................... 607/5, 7

[56] References Cited

U.S. PATENT DOCUMENTS

| | | | |
|---|---|---|---|
| 3,442,269 | 5/1969 | Oruz | 607/7 |
| 3,527,228 | 9/1970 | McLaughlin | 607/5 |
| 4,096,856 | 6/1978 | Smith et al. | 128/4.19 D |
| 4,610,254 | 9/1986 | Morgan et al. | 128/419 D |
| 4,619,265 | 10/1986 | Morgan et al. | 607/7 |

OTHER PUBLICATIONS

"Using the ForeRunner Biphasic AED", Heartstream, Inc., 1996.

*Primary Examiner*—William E. Kamm

[57] ABSTRACT

A dual-mode defibrillator has ECG electrodes connected to an ECG front end for producing signals for the controller to use in determining the defibrillator operation in accordance with the manual and automatic procedures stored in a memory. The controller provides appropriate signals to the high voltage delivery system which when energized, applies defibrillation energy to the electrodes.

6 Claims, 5 Drawing Sheets

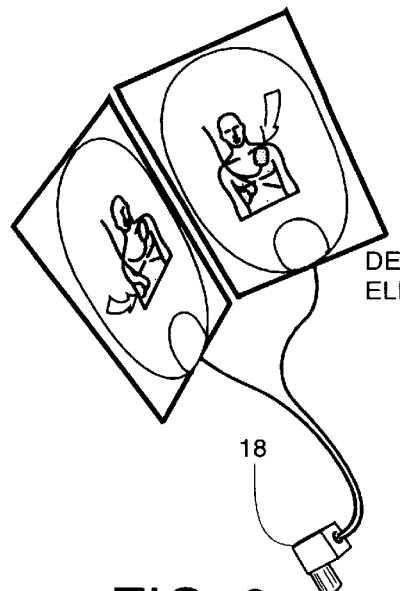
FIG. 3
DEFIBRILLATION ELECTRODES
16
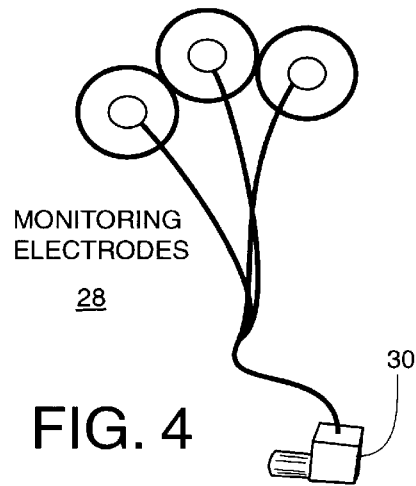
MONITORING ELECTRODES
28
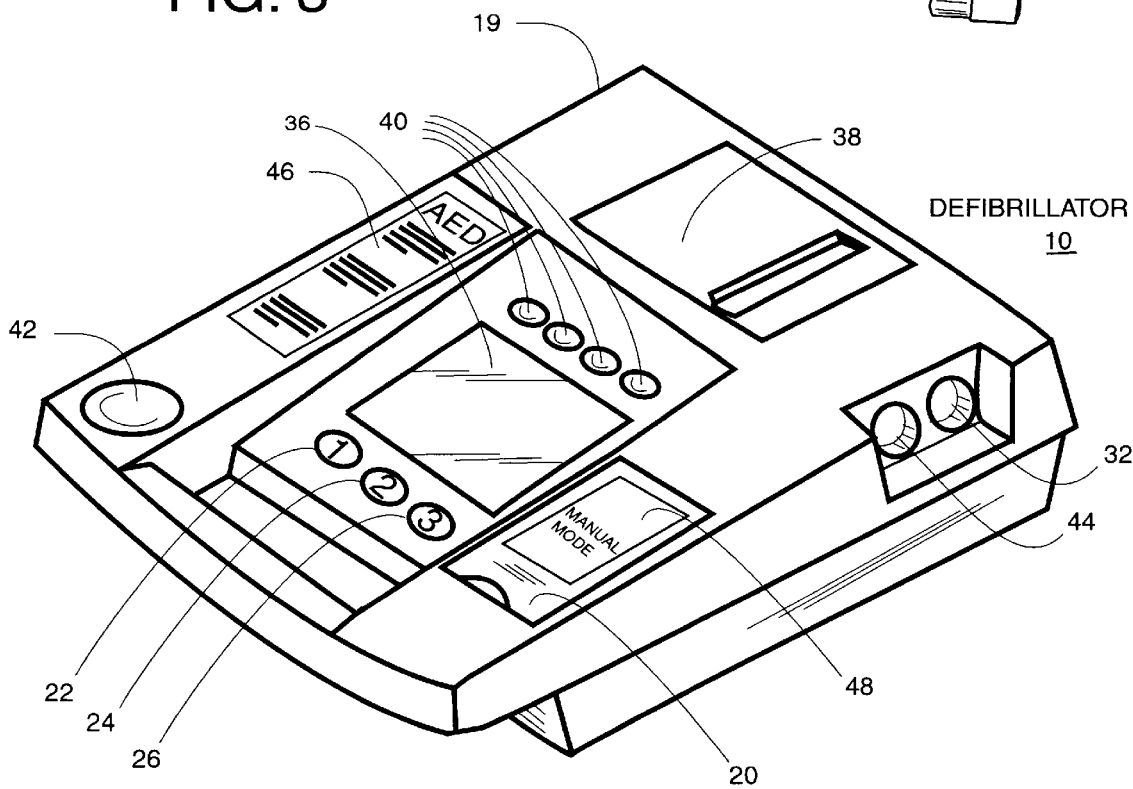
FIG. 2

DEFIBRILLATOR WITH AUTOMATIC AND MANUAL MODES

BACKGROUND OF THE INVENTION

This invention relates to medical equipment and in particular to a user interface for a defibrillator having separate manual and automated functions.

One frequent consequence of heart disease is the development of cardiac arrest associated with a heart arrhythmia, such as ventricular fibrillation. Ventricular fibrillation may be treated by delivering an electrical shock to the patient's heart through the use of a defibrillator. Cardiopulmonary resuscitation (CPR) is commonly used to maintain life support for victims of cardiac arrest until a defibrillator can be deployed to treat the arrhythmia.

The chances of surviving a cardiac arrest decrease rapidly over the time following the arrest. Quick response to a cardiac arrest by performing CPR and by administering a defibrillating shock is therefore of critical importance. The American Heart Association's "Chain of Survival" recites the following steps:

1. Early access to emergency care, such as by activating an emergency medical system (EMS);
2. Early CPR initiated by a bystander or other first responder using basic life support (BLS) techniques to help the patient survive until more advanced care arrives;
3. Early defibrillation; and
4. Early advanced cardiac care. The benefits of this approach are discussed in more detail in Cummins, et al. "Improving Survival From Sudden Cardiac Arrest: the 'Chain of Survival' Concept," 83 Circulation 1832–47 (May 1991).

EMS providers are playing an active role in implementing the Chain of Survival concept. Tiered EMS systems are emerging in many geographical areas, typically divided between first responders, BLS (basic life support) providers, and ACLS (advanced cardiac life support) providers, are emerging in many geographic areas. First responders and BLS providers, often called EMT(B) or EMT-basic, the front line personnel who are first to reach a patient, are now being trained and authorized to use automatic external defibrillators (AEDs) to provide early defibrillation.

AEDs deliver a high-amplitude current impulse to the heart in order to restore normal rhythm and contractile function in the patients who are experiencing ventricular fibrillation (VF) or ventricular tachycardia (VT) that is not accompanied by a palpable pulse. AEDs differ from manual defibrillators in that AEDs can automatically analyze the electrocardiogram (ECG) rhythm to determine if defibrillation is necessary. In nearly all AED designs, the first responder is prompted to press a shock button to deliver the defibrillation shock to the patient. Paramedic defibrillators often combine the AED and manual functions into one unit to allow for use by personnel with differing levels of training.

AEDs are designed to be used primarily by first responders who may not be trained in ACLS techniques. In the pre-hospital setting, these first responders may include emergency medical technicians trained in defibrillation (EMT-Ds), police officers, flight attendants, security personnel, occupational health nurses, and firefighters. AEDs can also be used in areas of the hospital where personnel trained in ACLS are not readily available. In such cases, it may be desirable to provide a paramedic defibrillator which operates in an AED mode with the manual functions disabled.

Having a simple, easily understood user interface in an AED is particularly important in applications where the first responder may have only infrequent need to use the AED. Because training and refresher courses may be relatively infrequent, coupled with a high stress emergency situation in which the AED is designed to be used in, the user interface design is therefore critical. A simple, interactive user interface for a AED is discussed in U.S. Pat. No. 4,610,254, "Interactive Portable Defibrillator", issued Sep. 9, 1986 to Morgan et al. and assigned to Physio-Control Corporation. The user interface taught by Morgan et al. prompts the operator with questions on an LCD display which are answered by pressing "YES" or "NO" buttons for interactive guidance through the patient analysis process. A separate button for "SHOCK" is pressed to deliver a defibrillation shock to the patient. The AED is automatically activated with the removal of the cover plate which exposes instructions placed on the underside of the cover plate.

In more recent AED designs such as the Heartstream Forerunner® defibrillator, the AED functions have been logically grouped into step 1, "power on"; step 2, "analyze"; and step 3, "shock." More sophisticated audio prompts have been added in addition to the visual prompts provided by the LCD display. The transition from step 1 to step 2 may be initiated by the defibrillator, such as upon detection of patient contact between the defibrillation electrodes to begin the ECG analysis as soon as possible. Proceeding from step 2 to step 3 according to the AED personality requires the user to press a shock button upon recognition of a shockable rhythm by the ECG analysis. In this way, the AED personality is commonly understood to mean semi-automatic rather than fully automatic defibrillation.

The step 1, 2, and 3 methodology, with some variation among manufacturers, is commonly understood and accepted as the AED personality. After step 3, the AED can continue the ECG analysis as a background process to watch for shockable rhythms and alert the user.

In many EMS systems, the next link in the Chain of Survival is provided with the arrival of ACLS trained paramedics on the scene equipped with full featured defibrillators/cardiac monitors ("paramedic defibrillators"). Alternatively, if no ACLS trained personnel are available, the patient is directly transported to a hospital emergency department where ACLS care can be provided. ACLS personnel typically use paramedic defibrillators which contain more advanced cardiac monitoring and analysis functions such as 3, 5, or 12 lead ECG monitoring, along with other functions such as cardiac pacing. These functions are manual functions requiring additional skill and judgment of the operator over that of the first responder.

The HP CodeMaster 100 defibrillator with shock advisory is an example of a manual defibrillator having AED functionality. While capable of performing dual roles both as an AED and a manual defibrillator, such a defibrillator may be not optimal for first responders. The manual and automatic modes are blended together on the same rotary switch on the front panel. The AED personality in such a defibrillator is designed more for a clinical environment for use by more skilled personnel and does not follow the more easily understood step 1-2-3 format outlined above.

It is desirable to have the ability to standardize on one type of defibrillator that may be used effectively by both first responder and ACLS personnel. Standardization helps to reduce the number and types of defibrillators in an EMS system in order to minimize support and administration costs. Because the training level and qualifications of BLS and ACLS personnel are different, the functions available on the defibrillator must necessarily be different. Therefore, it would be desirable to provide a defibrillator with an AED personality in terms of the step 1-2-3 format substantially maintained for the BLS personnel while logically segregating and restricting access to the manual functions to qualified ACLS personnel.

SUMMARY OF THE INVENTION

In accordance with the present invention, a defibrillator having separable AED and manual modes of operation is provided. The user interface of the defibrillator comprises a set of buttons for implementing the AED personality of step 1, step 2, and step 3, along with the associated audio and visual prompts. A separate input for connecting the defibrillation electrodes is provided. The user interface provides the appropriate audible and visual prompting to the user to connect the defibrillation electrodes to the patient.

The user interface also includes a set of manual buttons associated exclusively with the manual personality of the defibrillator. The manual buttons provide access to such functions as selecting the defibrillation energy level, activating synchronized cardioversion, pacing, and so on. Such functions are necessarily manual because of their relatively high complexity, large number of parameters to control, and high skill level required of the user to interpret the results. The manual personality defines the access to these manual functions with the defibrillator in manual mode and allows for an enhanced ability to select, configure, and control these functions.

In order to maintain the logical and physical separation of the AED and manual personalities, the manual keys are located underneath an access door on the top surface of the defibrillator. With the access door in a closed position, the defibrillator operates according to the AED personality. With the access door in the open position, manual access buttons may be pressed to place the defibrillator in manual mode so that it may be operated according to the manual personality. Alternatively, a sensor connected to the access door may be used to sense the open and closed positions of the access door to provide for switching between the AED and manual modes.

Instructions for the operation of the manual functions may be provided on the underside of the access door. In this way, the instructions are only visible to the user when the access door is in the open position to avoid confusion to the first responder who has no need to see these instructions.

It may be desirable to provide no access control to the manual personality other than with label affixed to the top side of the access door to the effect "manual mode." Such a label may be sufficient to prevent accidental access to the physical opening of the access door since the first responder has no motivation to activate the manual personality. Alternatively, access to the manual mode may be further controlled using a mechanical key lock or a software pass code, among other methods.

One feature of the present invention is to provide a defibrillator with manual and AED personalities.

Another feature of the present invention is to provide a user interface for a defibrillator in which AED and manual personalities are logically and physical separate.

A further feature of the present invention is to provide an access door for isolating access to the manual personality of a defibrillator Another feature of the present invention is to provide instructions for the manual features affixed to the underside of the access door which may be viewed only when the access door is in the open position to access the manual buttons.

Other features, attainments, and advantages will become apparent to those skilled in the art upon a reading of the following description when taken in conjunction with the accompanying drawings.

BRIEF DESCRIPTION OF THE DRAWINGS

FIG. 2 is an illustration of the defibrillator with an access door for the manual personality in a closed position according to the present invention;

FIG. 3 is an illustration (not to scale) of defibrillation electrodes for connection to the defibrillator of FIG. 2;

FIG. 4 is an illustration (not to scale) of monitoring electrodes for connection to the defibrillator of FIG. 2;

DETAILED DESCRIPTION OF THE INVENTION

Figure 1:
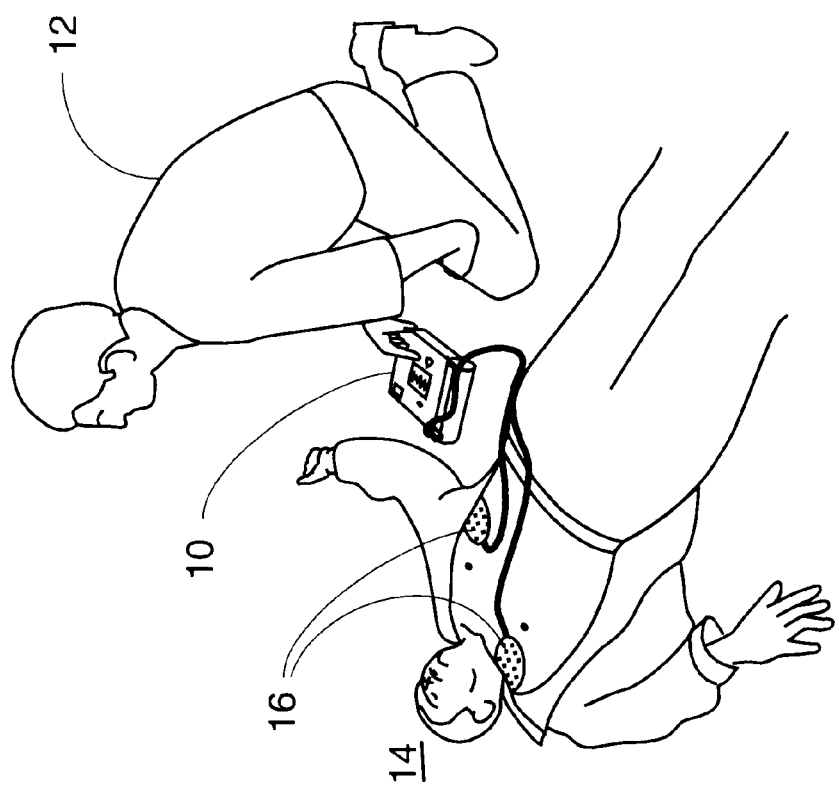
FIG. 1 is an illustration of a defibrillator being applied to a patient suffering from cardiac arrest.

FIG. 1 is an illustration of a defibrillator 10 being applied by a first responder 12 to resuscitate a patient 14 suffering from cardiac arrest. In cardiac arrest, otherwise known as sudden cardiac death, the patient is stricken with a life threatening interruption to their normal heart rhythm, typically in the form of ventricular fibrillation (VF) or ventricular tachycardia (VT) that is not accompanied by a palpable pulse. In VF, the normal rhythmic ventricular contractions are replaced by rapid, irregular twitching that results in ineffective and severely reduced pumping. If a normal rhythm is not restored quickly, a time frame commonly understood to be approximately 8 to 10 minutes, the patient 14 will die. Conversely, the quicker defibrillation can be applied after the onset of VF, the better the chances that the patient 14 will survive the event. Activating the EMS, typically with a telephone call to a local emergency telephone number such as 911 in North America, begins the process to obtain emergency treatment.

A pair of defibrillation electrodes 16 are applied across the chest of the patient 14 by the first responder 12 in order to acquire an ECG signal from the patient's heart. As first step, the defibrillator 10 is powered on and prompts the first responder 12 to attach the defibrillation electrodes 16 to the patient 14. The second step is the defibrillator 10, either initiated by a key press or by detecting patient contact with the defibrillation electrodes 16, automatically analyzes the ECG signal to detect a shockable rhythm such as ventricular fibrillation (VF). If VF is detected, the defibrillator 10, now at step three, prompts the first responder 12 that a shock is advised and to press the shock button to deliver the shock to resuscitate the patient 14.

Under the tiered EMS model, the patient 14 is handed off from the first responder to ACLS personnel who provide more advanced monitoring and cardiac care to the patient 14 with the defibrillator 10 in a manual personality. It is desirable that access to the manual functions be available in the same defibrillator 10 without compromising its ease of use with the AED personality to the first responder 12.

FIG. 2 is a more detailed illustration of the defibrillator 10 according to the present invention having an access door 20 shown in a closed position on a housing 19. On a top surface of the defibrillator 10 is located a power-on button 22 labeled "1" which powers up the defibrillator 10 and begins the process of the prompting the first responder 12 to connect the defibrillation electrodes 16 to the patient 14. Adjacent to the power-on button 22 is an analyze button 24 labeled "2" which initiates an automated analysis of the ECG signal acquired from the patient 24 which produces a shock advisory message. The ECG analysis may also be initiated automatically upon detection of patient contact across the defibrillation electrodes 16. Adjacent to the analysis button 24 is a shock button 26 labeled "3" which initiates delivery of the defibrillation shock to the patient 14 across the defibrillation electrodes 16 if shock is recommended by the ECG analysis. The power-on button 22, analysis button 24, and shock button 26 labeled "1", "2", and "3" collectively are AED buttons 34 which implement the AED personality. The precise labeling of the AED buttons 34 is not critical as long as the logical order of the AED personality is maintained to minimize confusion.

A display 36 mounted adjacent to the AED buttons 34 is preferably a liquid crystal display (LCD) that is capable of displaying text such as labels and graphics such as ECG traces. A printer 38 mounted on the top surface of the defibrillator 10 provides hard copy of ECG signals and event markers gathered during treatment of the patient 14. A set of softkeys 40 mounted adjacent to the display 36 provides for selection of functions according to softkey labels (not shown) on the display 36. A speaker 42 provides for audio prompts to the user, particularly when the defibrillator 10 is in AED mode. A connector 44 provides for coupling to other sensors gathering patient parameters such as pulse oximetry ($SpO_2$).

An AED instruction label 46 is mounted on the top surface of the defibrillator 10. The AED instruction label 46 provides an important part of the prompts to the first responder who must implement the step 1-2-3 process according to the AED personality.

A manual mode warning label 48 is mounted on a top side of the access door 20. The manual mode warning label 48 contains text or graphics designed to warn off the first responder 12 from opening the access door 20. For example, text that reads "MANUAL MODE" may be used if this label has sufficient meaning to the first responder 12 to prevent confusion in an emergency situation. Access to the manual mode personality can be further protected with a mechanical key lock (not shown) on the access door 20 or a software access code that must be entered on via a combination of button presses.

FIG. 3 is an illustration of the defibrillation electrodes 16 having a connector 18 for insertion into a patient connector socket (not shown) on a front surface of the defibrillator 10. The defibrillation electrodes 16 are used both to acquire the ECG signal from the patient 14 and to couple the defibrillation shock across the patient 14 from the defibrillator 10. The defibrillation electrodes 16 are selected automatically with the defibrillator 10 in the AED mode and may also be selected manually with the defibrillator 10 in manual mode.

FIG. 4 is an illustration of a set of monitoring electrodes 28 having a connector 30 for connection to a monitoring port 32 on the defibrillator 10. Three monitoring electrodes 28 are shown for purposes of illustration. Greater or fewer numbers of monitoring electrodes 28 may be chosen for various applications such as to implement 3, 5, or 12 lead ECG monitoring.

Figure 5:
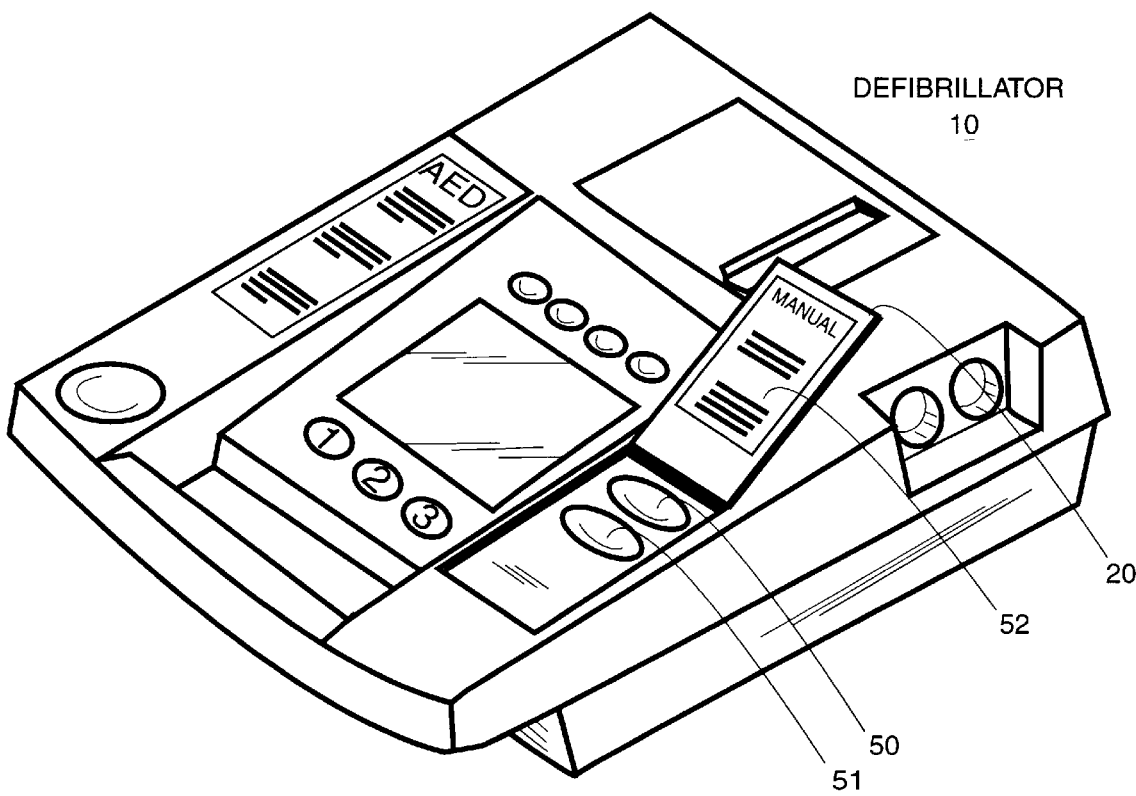
FIG. 5 is an illustration of the defibrillator with the access door for the manual personality in an open position according to the present invention.

FIG. 5 is a more detailed illustration of the defibrillator 10 according to the present invention having the access door 20 shown in an open position. A manual access button 50 controls access to the manual mode. In manual mode, various manual functions including synchronized cardioversion or pacing may be selected using a manual function select 51. Mounted on the bottom side of the access door 20 is a manual mode instruction label 52 that provides instruction to the ACLS user on manual mode operation. The manual access button 50, the manual function select 51, and the manual mode instruction label 52 are visible to the user only when the access door 20 is in the open position.

An alternative embodiment of the present invention provides for switching between the AED mode and the manual mode simply by opening the access door 20, thery7b eliminating the need to press the manual access button 50 to place the defibrillator 10 in the manual mode. A switch or sensor (not shown) may be coupled to the access door 20 to sense the open or closed position of the access door 20 to place the defibrillator 10 in the manual or AED modes respectively. The manual function select 51 located underneath the access door 20 would still be used to select among various manual functions including synchronized cardioversion and pacing with the defibrillator 10 in manual mode.

Figure 6:
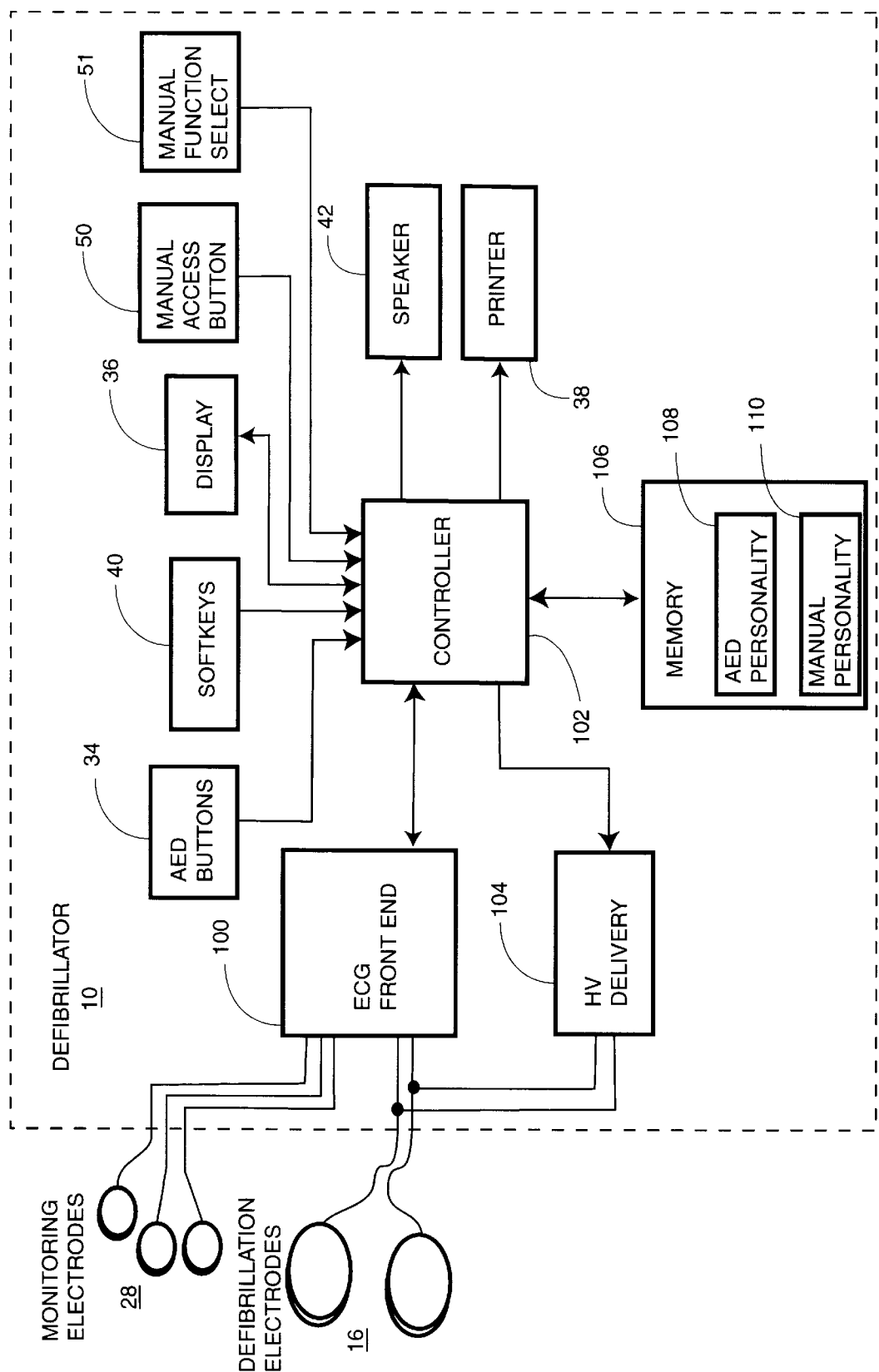
FIG. 6 is a simplified block diagram of the defibrillator of FIG. 2 according to the present invention.

FIG. 6 is a simplified block diagram of the defibrillator 10 according to the present invention. An ECG front end 100 is connected to the defibrillation electrodes 16 that are in turn connected across the chest of the patient 14. The ECG front end 100 operates to amplify, buffer, filter and digitize an electrical ECG signal generated by the patient's heart to produce a stream of digitized ECG samples. The digitized ECG samples are provided to a controller 102 which performs an ECG analysis to detect VF, VT or other shockable rhythm. If a shockable rhythm is detected, the controller 102 sends a signal to HV delivery 104 to charge up in preparation for delivering a defibrillation shock. Pressing the shock button 26 (shown in FIG. 2) then triggers the HV delivery 104 via the controller 102 to deliver a defibrillation shock to the patient 14 through the electrodes 16.

Also connected to the ECG front end 100 is the set of monitoring electrodes 28. The ECG front 100 is capable of selecting among the defibrillation electrodes 16 and the monitoring electrodes 28, preferably according to the controller 102.

The memory 106 may be implemented either as on-board RAM or ROM, a removable memory card, or a combination of different memory technologies. The memory 106 contains an AED personality 108 and a manual personality 110. The AED personality 108 defines the operation of the defibrillator 10 in AED mode, such as the operation of the AED buttons 34 and the content of what is displayed on the display 36. A manual personality 110 defines the operation of the defibrillator 10 in manual mode, such as the operation of the AED buttons 34, the softkeys 40, the manual function select 5 1, and the content of what is displayed on the display 36.

The AED buttons 34, softkeys 40, display 36, speaker 42, printer 38, manual access button 50, and manual function select 51 collectively form the user interface of the defibrillator 10 and are connected to the controller 102 to receive input from the user and provide audio and visible feedback to the user. Dedicated buttons, such as to control the printer operator or to adjust the ECG size, display contrast, and speaker volume, may be included to control common functions of the defibrillator 10 in both AED and manual modes in the preferred embodiment.

Figures 7A, 7B:
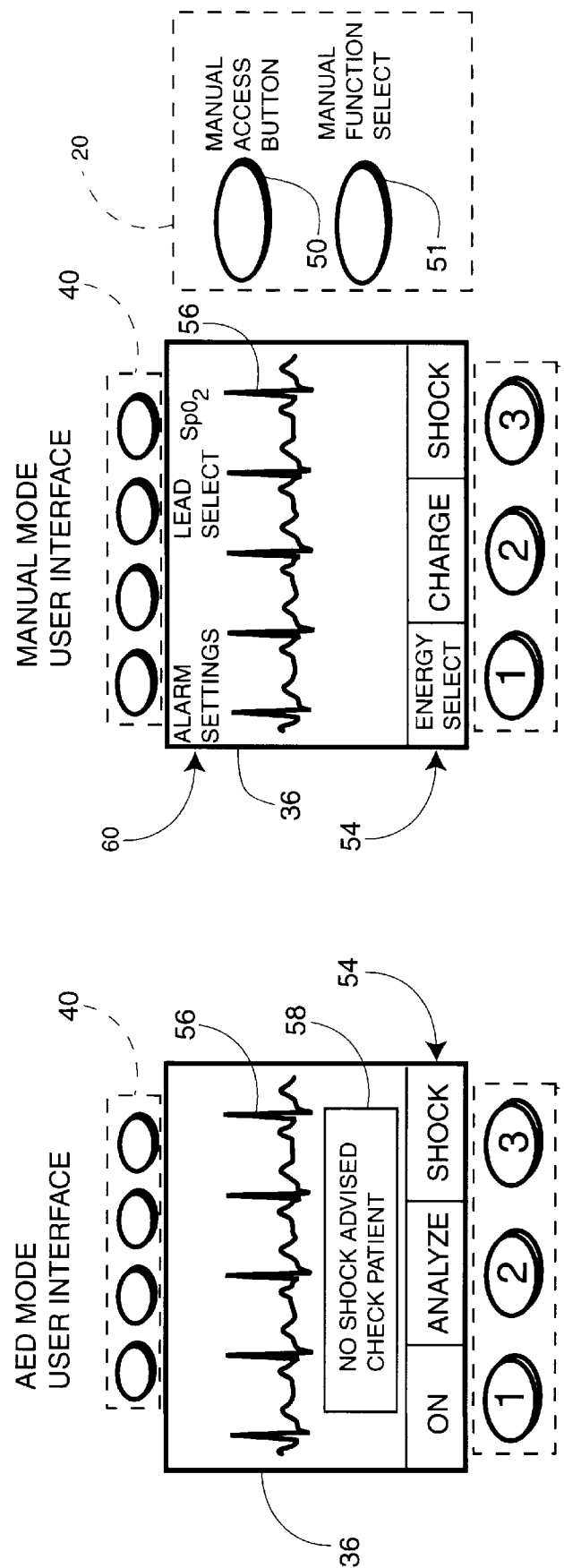
FIG. 7A and 7B is a diagram of a user interface of the defibrillator in AED mode and in manual mode employing a graphical display device and associated softkeys to implement the AED personality.

FIG. 7A and 7B are illustrations of the selected portions of the user interface of the defibrillator 10 in AED mode and manual mode respectively. In FIG. 7A, with the defibrillator 10 in AED mode, the AED buttons 34 for operating the defibrillator 10 are labeled by a set of soft labels 54 including "ON", "ANALYZE", and "SHOCK" which define their functions according to the AED personality 108. A graphical trace 56 of the ECG signal may be displayed in the center portion of the display 36. A message block 58 containing selected user prompts such as "NO SHOCK ADVISED CHECK PATIENT" may be placed on the lower portion of the display 36. The softkeys 40 may be configured to be on or off with the defibrillator 10 depending on the particular version of the AED personality 108 that has been chosen. In some EMS systems, none of the softkeys 40 may be enabled while in other EMS systems, a selected set of functions may be made available with the defibrillator in AED mode.

In FIG. 7B, the manual access button 50, which is revealed by opening the access door 20, may be pressed to place the defibrillator 10 into the manual mode. In the manual mode, the set of soft labels 54 are changed as functions controllable by the more advanced ACLS user are added to the menu structure in manual mode according the manual personality 110. As shown, the set of soft labels 54 now read "ENERGY SELECT", "CHARGE", and "SHOCK" which define the functions of the AED buttons 34 in their operation of the defibrillator in the manual mode. Various manual functions such as synchronized cardioversion or pacing may be selected with the manual function select 51 which is also located under the access door 20 to avoid confusion with the AED buttons 34. In addition, the softkeys 40 may be activated to reveal a set of soft labels 60 including, for example, "ALARM SETTINGS", "LEAD SELECT", and "SpO$_2$" which are added to label the functions of each of the softkeys 40 for additional user control of manual functions according to the manual personality 110. Menu trees may be implemented and logically arranged to provide ready access to the desired manual functions available according to the manual personality 110.

It will be obvious to those having ordinary skill in the art that many changes may be made in the details of the above-described preferred embodiments of the invention without departing from the spirit of the invention in its broader aspects. A variety of physical and mechanical means may be devised for concealing and physically separating the manual mode functions while preserving the AED functions needed by the first responder. For example, the manual access button 50 can be placed on another portion of the housing 19 of the defibrillator 10 such on a side or rear portion which is not readily visible to the first responder. Therefore, the scope of the present invention should be determined by the following claims.

We claim as our invention is:

1. A defibrillator comprising:
   ECG electrodes for coupling to a patient;
   an ECG front end coupled to said ECG electrodes for receiving an ECG signal from said patient;
   a controller coupled to said ECG front end to receive said ECG signal and detect a shockable rhythm;
   memory coupled to said controller, said memory containing an AED personality and a manual personality;
   AED buttons for operating said defibrillator according to said AED personality in an AED mode;
   HV delivery for coupled to said controller and to said AED electrodes for delivering a defibrillation shock to said paid responsive to said AED buttons; and
   manual access button for placing said defibrillator into a manual mode for operation according to said manual personality.

2. A defibrillator according to claim 1 further comprising an access door covering said manual access button wherein said manual access button may be accessed only when said access door is in an open position.

3. A defibrillator according to claim 2, said access door comprising a top side and a bottom side, and a manual mode warning label mounted on said top side.

4. A defibrillator according to claim 3, said access door further comprising a manual mode instruction label mounted on said bottom side.

5. A defibrillator according to claim 1 further comprising softkeys for operating said defibrillator according to said manual personality.

6. A defibrillator according to claim 5 further comprising monitoring electrodes wherein said ECG front end selects said monitoring electrodes responsive to said softkeys.

* * * * *

UNITED STATES PATENT AND TRADEMARK OFFICE
CERTIFICATE OF CORRECTION

| | |
|---|---|
| PATENT NO. | : 6,021,349 |
| APPLICATION NO. | : 09/126905 |
| DATED | : February 1, 2000 |
| INVENTOR(S) | : Patricia A. Arand et al. |

It is certified that error appears in the above-identified patent and that said Letters Patent is hereby corrected as shown below:

In Claim 1, Column 8, line 23, cancel "coupled" and replace with:

--coupling--

In Claim 1, Column 8, lines 23-24, cancel "said AED electrodes" and replace with:

--said ECG electrodes--

In Claim 1, Column 8, line 25, cancel "said paid" and replace with:

--said patient--

Signed and Sealed this

Twenty-ninth Day of June, 2010

David J. Kappos
*Director of the United States Patent and Trademark Office*